United States Patent [19]

Roberts

[11] Patent Number: 4,994,624

[45] Date of Patent: Feb. 19, 1991

[54] PROCESS FOR PREPARING ORGANOTHIOALKANOLS

[75] Inventor: John S. Roberts, Bartlesville, Okla.

[73] Assignee: Phillips Petroleum Company, Bartlesville, Okla.

[21] Appl. No.: 464,848

[22] Filed: Jan. 16, 1990

Related U.S. Application Data

[63] Continuation of Ser. No. 224,092, Jul. 26, 1988, abandoned.

[51] Int. Cl.$^5$ ............................................. C07C 319/14
[52] U.S. Cl. ...................................................... 568/55
[58] Field of Search ....................... 568/55; 203/18, 70

[56] References Cited

U.S. PATENT DOCUMENTS 3,575,818  4/1971  West ......................................... 203/70
4,161,429  7/1979  Baiel et al. ............................. 203/70

OTHER PUBLICATIONS

Chemical Abstracts, vol. 74, 1971, p. 344, Abstract No. 146819y, Draiko, L. I., "Pressure Dependence of Composition and Boiling Point of Binary Heteroazeotropes".

Journal of the American Chemical Society, vol. 88, Sep. 5, 1966, pp. 3982-3995, G. Lienhard et al.

Levi, T. G., Gazetta Chimica Italiana, vol. 62, 1932, pp. 775-780 (translation included).

Derwent Abstract of U.S.S.R., Patent No. 263,593, published May 15, 1970.

*Primary Examiner*—Mary E. Ceperley
*Attorney, Agent, or Firm*—Richmond, Phillips, Hitchcock & Umphlett

[57] ABSTRACT

Organothioalkanols are prepared by reacting a mercaptan with an aldehyde or ketone. Reaction impurities, such as water, are removed to enhance product stability.

14 Claims, No Drawings

PROCESS FOR PREPARING ORGANOTHIOALKANOLS

This application is a continuation of pending application Ser. No. 07/224,092, filed July 26, 1988, now abandoned.

BACKGROUND OF THE INVENTION

This invention relates to a method for making organothioalkanols.

It is known in the art to react mercaptans, or thiols, with aldehydes or ketones to produce organothioalkanols according to the general equation:

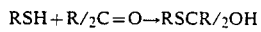

Each R or R/ can be the same or different species selected from the group consisting of straight chain or branched hydrocarbons and/or hydrogen. Unfortunately, product yields are usually relatively low and, due to reaction impurities, the desired reaction product is usually unstable. These reaction impurities can be solvents or other impurities in the reactants and/or reaction by-products. For example, formaldehyde, which can be one of the reactants, is commonly available in an aqueous solution and stabilized with a minor amount of methanol. Thus, water can be present with the reaction products.

Removal of the reaction impurities can have a deleterious effect on the reaction product; i.e., the desired organothioalkanol can be destroyed if the reaction impurities are removed in an improper manner. However, it is advantageous to remove the reaction impurities to enhance the stability of the desired reaction product. One method to remove water is to employ vacuum oven stripping. Unfortunately, this method of water removal can be detrimental to the desired reaction product.

SUMMARY OF THE INVENTION

It is an object of this invention to provide a novel process to produce organothioalkanols.

It is another object of this invention to provide a process to produce organothioalkanols with an improved product yield.

It is yet a further object of this invention to provide an improved process to purify and stabilize organothioalkanols.

In accordance with this invention, mercaptans of the general formula RSH, wherein R is an aliphatic radical having from about 1 to about 24 carbon atoms, are refluxed with an aliphatic oxygen-containing compound selected from the group consisting of aldehydes and ketones having less than or equal to about 18 carbon atoms, for a time and at a temperature sufficient to form an organothioalkanol.

In accordance with another embodiment of this invention, substantially all water is removed from the organothioalkanol reaction product.

DESCRIPTION OF THE PREFERRED EMBODIMENTS

Organothioalkanols can be used in a variety of applications, such as, for example, intermediates in pesticide production. A process which produces a relatively stable product with a relatively high product yield of organothioalkanols is preferred, to economically and effectively use reactants and reagents.

The term "organothioalkanol", as used in this disclosure, is defined by the general formula $RSCR/_2OH$. Each R or R/ can be the same or different species selected from the group consisting of straight chain or branched hydrocarbons and/or hydrogen.

REACTANTS

The mercaptan compounds, also called thiol compounds, suitable for use in this invention to prepare organothioalkanols are aliphatic mercaptans, having the general formula RSH, wherein R is a straight chain or branched aliphatic hydrocarbon radical having from about 1 to about 24 carbon atoms. Preferably, the aliphatic hydrocarbon radical has from about 1 to about 10 carbon atoms and most preferably from about 1 to about 6 carbon atoms. Lower molecular weight organothioalkanols are generally less stable than higher molecular weight organothioalkanols; this invention is particularly applicable to providing a process to produce more stable lower molecular weight organothioalkanols.

Suitable mercaptan compounds include, but are not limited to, t-butyl mercaptan, methyl mercaptan, ethyl mercaptan, n-propyl mercaptan, isopropyl mercaptan, n-butyl mercaptan, sec-butyl mercaptan, isobutyl mercaptan, 1-pentanethiol, 4-methyl-1-butanethiol, 2-methyl-2-butanethiol, 2-methyl-1-butanethiol, 2-methyl-1-pentanethiol, 3-methyl-2-pentanethiol, 2-methyl-3-pentanethiol, 2,3-dimethyl-1-butanethiol, 2,3-dimethyl-2-butanethiol, 2-ethyl-1-butanethiol, 2-ethyl-2-butanethiol, 1-heptanethiol, 2-methyl-1-hexanethiol, 4-methyl-3-hexanethiol, 2,2-dimethyl-1-pentanethiol, 1-octanethiol, 2,4,4-trimethylpentanethiol, t-octylmercaptan, t-nonylmercaptan, 1-decanethiol, 2-decanethiol, and mixtures thereof. Preferably, methyl mercaptan, ethyl mercaptan, n-propyl mercaptan, isopropyl mercaptan, n-butyl mercaptan, t-butyl mercaptan, 1-octanethiol, and mixtures thereof are used because of commercial availability and usefulness to produce the desired resultant products.

The aliphatic oxygen-containing compounds suitable for use in this reaction are linear and branched aliphatic compounds selected from the group consisting of ketones and aldehydes with less than or equal to about 18 carbon atoms. Preferably, the oxygen-containing compound has from about 1 to about 12 carbon atoms, and most preferably from about 1 to about 6 carbon atoms due to commercial availability and ease of use of the reactants.

Suitable linear or branched aliphatic ketones and linear or branched aliphatic aldehydes include, but are not limited to, formaldehyde, acetone, methyl ethyl ketone, methyl isopropyl ketone, methyl t-butyl ketone, methyl isobutyl ketone, 2-pentanone, 3-pentanone, ethyl isopropyl ketone, 5-methylhexan-3-one, 2-methylheptan-3-one, 2-hexanone, 3-hexanone, 2-heptanone, 3-heptanone, 4-heptanone, 2-octanone, 3-octanone, 4-octanone, ethyl t-butyl ketone, methyl t-amyl ketone, methyl sec-amyl ketone, methyl sec-butyl ketone, formaldehyde, acetaldehyde, propionaldehyde, n-butanal, 2-methylpropanal, 2-methylbutanal, 3-methylbutanal, 2,2-dimethylbutanal, 2,3-dimethylbutanal, 3,3-dimethylbutanal, pentanal, 2-methylpentanal, 3-methylpentanal, 4-methylpentanal, 2,2-dimethylpentanal, 2,3-dimethylpentanal, 3,3-dimethylpentanal, 2,4-dimethylpentanal, 3,4-dimethylpentanal, 4,4-dimethylpentanal, heptanal, octanal, nonanal, and mixtures thereof.

Preferred linear or branched aliphatic ketones and linear or branched aliphatic aldehydes because of less steric hindrance include, but are not limited to, formaldehyde, acetone, methyl ethyl ketone, methyl isopropyl ketone, methyl isobutyl ketone, 2-pentanone, 2-hexanone, 2-heptanone, 2-octanone, acetaldehyde, propionaldehyde, n-butanal, pentanal, and mixtures thereof. The especially preferred oxygen-containing compound is formaldehyde.

The reactants can be present in the reaction vessel in any quantity. For best reactant use and reaction rate efficiency, the reactants are combined in a molar ratio of mercaptan to oxygen-containing compound in the range of about 3:1 to about 0.1:1, preferably in the range of about 2:1 to about 0.5:1. Most preferably, the reactants are combined in a molar ratio of mercaptan to oxygen-containing compound in the range of about 1.3:1 to about 0.7:1 for best product yield and best conversion to the resultant organothioalkanol. This inventive process proceeds very well at about a 1:1 ratio of the reactants.

The reactants can be added to the reaction vessel in any order. If desired, the reactants can be in a diluent; however, use of a diluent can decrease the reaction efficiency. Water can be used as a diluent, but water is not preferred as a diluent because it can alter the reaction equilibrium. Water preferably is not affirmatively added to the reaction vessel. If a diluent is desired, inert hydrocarbons are preferred. In the context of this invention, inert hydrocarbons are defined as anything that will not react with the reactants or reaction products. Thus, compounds that do not react with oxygen-containing compounds and/or mercaptans are acceptable diluents. Inert hydrocarbon diluents include, such as, for example, pentane, hexane, cyclohexane, and mixtures thereof. Examples of compounds which have a detrimental effect on the reaction and are, therefore, unacceptable diluents include, but are not limited to, esters and acids, especially organic acids.

Preferably, the contents of the reaction vessel are maintained at a neutral to slightly basic pH, by any method known in the art, to avoid production of undesirable reaction products. Usually, the pH is maintained in the range of about 6 to about 9 and preferably in the range of about 7 to about 9 for best yields of the desired reaction products.

REACTION CONDITIONS

After addition to the reaction vessel, the reactants are refluxed for a time and at a temperature sufficient to cause the reaction to go to completion and form an organothioalkanol. The reaction is complete when reactants are depleted as shown by gas chromatography or any other suitable method.

The reaction to produce an organothioalkanol can be carried out using either batch or continuous operation, although the invention is particularly well suited for batch operation. Suitable equipment, such as reaction vessels, tubes, valves, and the like are well known in the art and can be employed. No special materials of construction for the reaction vessels are required, so that glass, stainless steel, glass-lined vessels, or other relatively non-reactive equipment can be employed.

Generally, sufficient refluxing time is in the range of about 1 to about 10 hours, preferably in the range of about 2 to about 8 hours. Most preferably, the reaction will be complete within a time in the range of about 2 to about 4 hours, depending on the reactants employed and the reflux temperature. The reflux temperature is generally in the range of about 30° to about 100° C. The specific reflux temperature depends on what reactants are employed.

Refluxing can occur under any type of atmosphere. For convenience, air is usually present in the reaction vessel.

During the refluxing process, the reaction vessel can be stirred or agitated, if desired, by any suitable method. Preferably, the reaction vessel is stirred during refluxing to effectuate better contact among the reactants.

After refluxing, the reaction vessel, which contains a reaction mixture comprising primarily reaction products, is allowed to cool by any method known in the art. For example, the mixture can be allowed to set to come to an ambient temperature, or the mixture can be cooled by use of cooling coils. Again, stirring is not necessary, but stirring can expedite the cooling process. The reaction mixture can be cooled at any convenient rate.

PRODUCT PURIFICATION

After sufficient cooling, undesirable reaction by-products, such as water, can be removed by any means known in the art. For example, an azeotropic solvent can be added to the reaction mixture to facilitate water removal. Any appropriate solvent which is insoluble in water and in which the desired reaction product is soluble can be used. Exemplary azeotropic solvents include, but are not limited to, pentane, cyclohexane, hexane, heptane, benzene, and octane. Preferably pentane, cyclohexane and hexane are used due to ease of use and commercial availability. If an azeotropic solvent is used, excess water can be removed by phase separation and residual water can be removed by azeotropic distillation.

If an azeotropic solvent is employed to remove excess water, the reaction mixture is preferably cooled to a temperature below about the boiling point of the azeotropic solvent. For example, if pentane is added to facilitate water removal, the reaction mixture is cooled to less than about 35° C., about the boiling point of pentane, after completion of refluxing, yet prior to the addition of pentane.

Finally, if desired, the azeotropic solvent can be removed. The azeotropic solvent can be removed by any method known in the art. For example, the azeotropic solvent can be removed with a slight vacuum. If more rapid solvent removal is desired, some of the azeotropic solvent can be removed by distillation. However, the distillation temperature preferably is maintained relatively low so as not to degrade, or heat stress, the desired reaction product. If, and when, the distillation temperature becomes higher than desired, heat can be removed and a slight vacuum can be applied to remove any excess azeotropic solvent.

EXAMPLES

Examples provided are intended to assist in a further understanding of the invention. Particular materials and conditions employed are intended to be further illustrative and not limitative of the reasonable scope of the invention.

COMPARISON

To a 5 L 3-necked round bottom flask fitted with mechanical stirrer, condenser and thermowell was added 1170 g (13 moles) t-butylmercaptan, 1027 g (13 moles) of 37% aqueous formaldehyde (10% methanol stabilized) and 1300 ml of methanol. The mixture was stirred, and heated to reflux at about 60° C. for 2.5 hours followed by cooling to 49° C. Upon addition of 715 ml water to the cooled reaction mixture, a second layer formed where the product was in the top layer; the top layer was removed. The bottom layer was extracted with 1000 ml of diethyl ether. The ether layer and previous product layer were pooled forming a water layer which separated from the original product layer; the water layer was discarded. The ether layer, now containing all product, was distilled on a 20"×1' Vigreaux column at atmospheric pressure to remove ether. After the evaporation was completed, residual water was removed at reduced pressure (40 mm Hg).

The resulting product weighed 1560 g, representing a yield of 65.4% (of theoretical). Gas chromatographic analysis (12'×⅛" stainless steel column containing 3% OV-101 on Chromosorb W; 50° to 300° C. at 15° C./min; TC detector) showed the product was 90% pure. Further instrumental analyses done by elemental analysis, IR, and NMR spectroscopy showed the product was t-butylthiomethanol.

The procedure described above was adopted from that disclosed by T. G. Levi (Gazz Chim. Ital., 62:775–780 (1932)). A series of t-butylthiomethanol preparations was made employing this process.

However, it was found that the products were very unstable, i.e., completely decomposed or reverted to the reactants, t-butylmercaptan and formaldehyde, in 2–3 days, demonstrated by gas chromatography described above. It is, therefore, concluded that development of a new process capable of producing a stable organothioalkanol was needed.

EXAMPLE

To a 5 L 3-necked round bottom flask, same as described in the Control, was added 900 g (10 moles) of t-butylmercaptan and 790 g (10 moles) of 37% aqueous formaldehyde (10% methanol stabilized). The flask was stirred and heated to reflux at about 60° C. for 2.5 hours. The mixture was then cooled to room temperature (25° C.) followed by addition of 900 ml of pentane. After phase separation was complete, the water (bottom) layer was discarded. The flask was then fitted with a Dean-Stark trap and excess water was removed by azeotropic distillation. A total of 161 ml water was removed by this distillation. The pentane (710 ml) was then removed by further distillation at atmospheric pressure till the reaction mixture reached 81° C. The remaining pentane was evaporated by vacuum distillation at 150 mm Hg at temperatures up to 61° C.

The resulting product weighed 1008 g, representing 84.0% yield (of theoretical). Analyses (GC, IR, NMR, and elemental) showed the product was t-butylthiomethanol.

The stability of product was determined by maintaining a set of samples at room temperature and in a refrigerator (4° C.) and by analyzing these samples periodically. Little change of product was found up to about three months suggesting the product made by this inventive procedure is far superior to that disclosed in the Control. Additionally, the results shown in this Example indicate a higher yield (84.0% vs. 65.4%) than that described in the Control and again demonstrate the inventive process is a superior method for preparing an organothioalkanol.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A process for producing a stable tertiary aliphatic thioalkanol comprising:
   (a) refluxing a tertiary aliphatic mercaptan having from about 1 to about 24 carbon atoms and an aliphatic oxygen-containing compound selected from the group consisting of aldehydes and ketones having less than or equal to about 18 carbon atoms;
   (b) for a time and at a temperature sufficient to form a tertiary aliphatic thioalkanol reaction product;
   (c) adding a water-insoluble organic solvent to said tertiary aliphatic thioalkanol reaction product to form a mixture; and wherein substantially all water is removed by
   (d) discarding the resulting water layer,
   (e) azeotropically distilling the remaining layer, and
   (f) recovering a stable tertiary aliphatic thioalkanol reaction product.

2. A process according to claim 1 wherein said tertiary aliphatic mercaptan has from about 1 to about 10 carbon atoms.

3. A process according to claim 1 wherein said tertiary aliphatic mercaptan is selected from the group consisting of t-butyl mercaptan, t-octylmercaptan, t-nonylmercaptan, and mixtures thereof.

4. A process according to claim 1 wherein said tertiary aliphatic mercaptan is t-butyl mercaptan.

5. A process according to claim 1 wherein said aliphatic oxygen-containing compound has from about 1 to about 12 carbon atoms.

6. A process according to claim 1 wherein said aliphatic oxygen-containing compound is selected from the group consisting of formaldehyde, acetone, methyl ethyl ketone, methyl isopropyl ketone, methyl isobutyl ketone, acetaldehyde, propionaldehyde, n-butanal, pentanal and mixtures thereof.

7. A process according to claim 1 wherein said aliphatic oxygen-containing compound is formaldehyde.

8. A process according to claim 1 wherein said time for refluxing is in the range of about 1 to about 10 hours.

9. A process according to claim 1 wherein said temperature for refluxing is in the range of about 30° to about 100° C.

10. A process according to claim 1 wherein the molar ratio of said mercaptan to said oxygen-containing compound is in the range of about 3:1 to about 0.1:1.

11. A process for producing stable t-butylthiomethanol comprising:
   (a) refluxing t-butyl mercaptan and formaldehyde;
   (b) at about 60° C. for about 2.5 hours to form t-butylthiomethanol;
   (c) adding pentane to said t-butylthiomethanol to form a mixture and wherein substantially all water is removed by
   (d) discarding the resulting water layer,
   (e) azeotropically distilling the remaining layer,
   (f) recovering a stable t-butylthiomethanol reaction product.

12. A process according to claim 1 wherein said azeotropic solvent is selected from the group consisting of pentane, cyclohexane, hexane, heptane, benzene and octane.

13. A process according to claim 1 wherein said solvent is pentane.

14. A method according to claim 11 which consists essentially of steps a to f.

* * * * *